United States Patent
Musikanti et al.

[11] Patent Number: 5,114,343
[45] Date of Patent: May 19, 1992

[54] RESILIENT SUPPORT STRUCTURE

[75] Inventors: Barry L. Musikant; Allan S. Deutsch, both of New York, N.Y.

[73] Assignee: Essential Dental Systems, Inc., Hackensack, N.J.

[21] Appl. No.: 573,568

[22] Filed: Aug. 27, 1990

[51] Int. Cl.⁵ .................. A61C 8/00; A61C 13/28
[52] U.S. Cl. .................. 433/173; 433/169; 433/174
[58] Field of Search .......... 433/172, 173, 174, 175, 433/177, 169

[56] References Cited

U.S. PATENT DOCUMENTS

| | | | |
|---|---|---|---|
| 3,717,931 | 2/1973 | Konig | 433/177 |
| 3,722,094 | 3/1973 | Rivoir | 433/169 |
| 3,863,344 | 2/1975 | Pillet | 433/173 |
| 4,657,510 | 4/1987 | Gittleman | 433/173 |
| 4,731,085 | 3/1988 | Koch | 623/16 |
| 4,957,437 | 9/1990 | Shimura et al. | 433/169 |
| 5,002,488 | 3/1991 | Homsy | 433/169 |
| 5,049,073 | 9/1991 | Lauks | 433/173 |

Primary Examiner—Eugene Mancene
Assistant Examiner—Cindy A. Cherichetti
Attorney, Agent, or Firm—Gottlieb, Rackman & Reisman

[57] ABSTRACT

A dental support structure for crown restoration which may be screwed into a hollow dental implant. The support structure has a stem which is adapted to receive a crown and which is moveable along the axis of the support structure in resistance to spring pressure and whose axis may tilt without substantial resistance from said spring pressure.

3 Claims, 1 Drawing Sheet

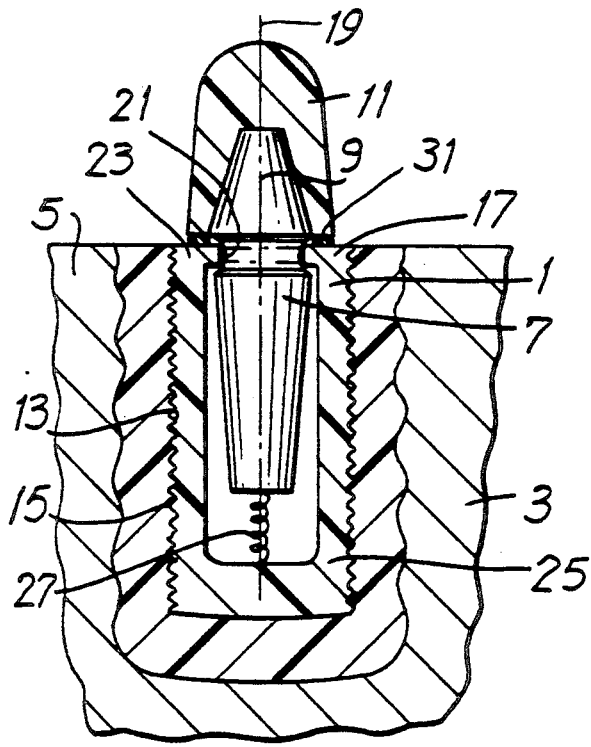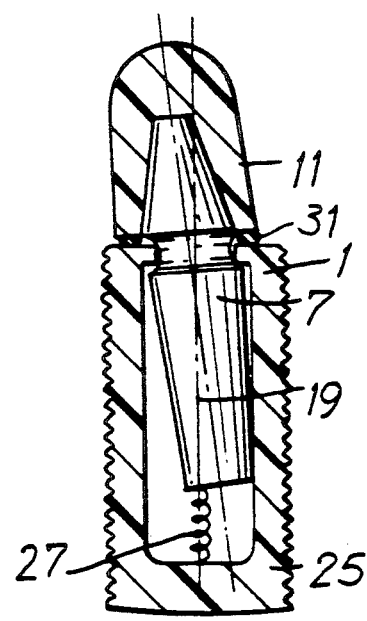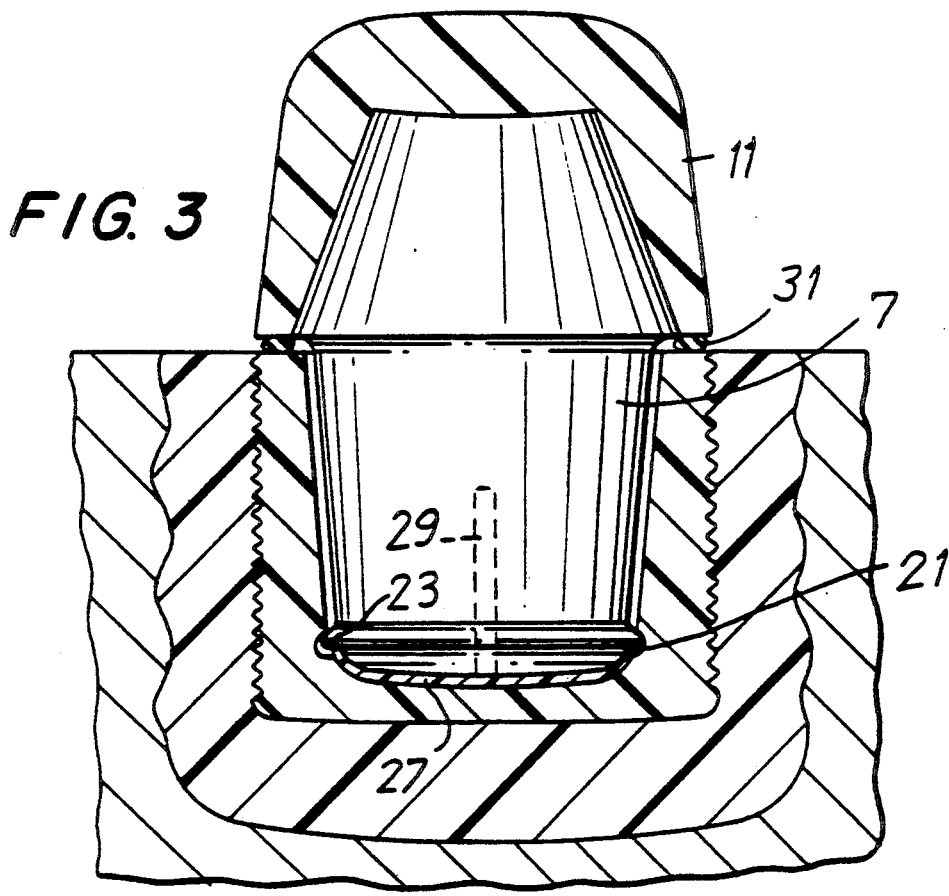

RESILIENT SUPPORT STRUCTURE

BACKGROUND OF THE INVENTION

This invention relates to an improved dental support structure for crown restoration used in conjunction with a dental implant when the tooth root is no longer present in the patient's gum.

Our prior U.S. Pat. No. 4,480,997 disclosed a new dental post that was adapted for thread cutting insertion into a tooth root. The invention of that patent divided the stem of the dental post into a plurality of legs moveable relative to each other. When inserted, the dental post was rigidly affixed to the tooth by screwing and/or using an adhesive. Such an implant was suitable where the tooth root was intact in the gum.

Where the tooth root is not present it has been customary to employ an implant which is fixed in relation to the jaw bone or has only the limited amount of motion which the implant experiences. It has also been known to provide some resiliency to the implant to prevent fractures of the implant or lysis of the retaining portion of the jawbone. For example, U.S. Pat. No. 4,793,808 employed a support structure that was itself elastomeric. U.S. Pat. No. 3,863,344 also disclosed an implantable dental support surrounded by an elastic material for cushioning on its sides. It included a stainless steel pin within an elastomeric envelope and resting on an elastomeric base, all within a textile sleeve. This reduced the pressure on the bone of the jaw to reduce lysis, but was not specifically designed to provide the degree of motion simulating the motion of a natural tooth.

U.S. Pat. No. 4,731,085 disclosed an enossal implant made of fragile thin walled alumina ceramics for insertion in a jawbone. The implant was designed with a complex internal structure to cushion the torques that could fracture the thin walls and brittle structures of the implant. It provided, in each of several embodiments, a series of elastomeric sleeves surrounding a central cylinder so that sidewise, i.e., lateral torques were cushioned. A complex structure involving close fitting sleeves and machined surfaces allowed some translational motion limited in such a way as to reduce strain. The elastic structures were not designed to provide the feel of a natural tooth, but rather to shift the fulcrum of motion to predetermined locations as compression increased, in order to control torques.

The present invention provides the advantage of toothlike degrees of freedom without the complexity of the prior art by providing an essentially unrestrained off axis movement of the dental support structure within the implant and locating the elastic medium at an extremity of the support structure.

BRIEF DESCRIPTION

The present invention uses an implant which contains a dental support structure that is resiliently moveable with respect to the portion of the implant that contacts the gum in a manner simulating a natural tooth. This allows a limited degree of controlled movement of the anchoring portion of a dental support structure (i.e. the portion to which the restored crown is attached) when the patient bites down upon the restored crown. The result is a more normal feel of the restored tooth to the patient. Furthermore the durability of the implant and crown is improved when the attached crown is not immovably connected to the patient's jaw, but has a certain amount of give which is controllable by the patient's bite. The design allows greater thickness to the support structure than in the prior art where diameters had to be reduced to allow for the insertion of cushioning material. The result is a dental support structure that is optimized for patient comfort while providing sufficient durability.

Natural tooth roots are attached to the gum by anatomic structures that make up the periodontal ligament. These structures control the forces that are transmitted from the teeth to the supporting bone. This periodontal ligament is a dense connective tissue which mediates between the root and the alveolar bone. It has a width which ranges from 0.15 to 0.38 mm and which varies in response to occlusal loading. Dentoalveolar fiber bundles occupy most of the periodontal ligament volume. The structure of these bundles is quite complex with the fiber bundles arranged into networks having complex three-dimensional overlapping configurations. During mastication the teeth contact and engage in a substantial amount of lateral gliding contact that produces both axial and horizontal loads. Because of the periodontal ligament this results in tooth movement in all directions.

The relationship between the force exerted on a tooth and its displacement is nonlinear, but has been described as a continuous curve made up of three linear components, Muhlemann, H. R. Periodontometry: A method for measuring tooth mobility. Oral Surg. 4:1220, 1951, as well as by more complex logarithmic functions. The threefold linearity allows an intial relatively free phase followed by progressively less mobile phases. The break points, i.e., the points at which the scope of the curve changes suddenly are at about 1.0N and 15.0N.

Teeth normally have the ability to move and such movement is important in allowing the discrimination of size, shape, texture and hardness of objects being bitten. In addition, the sensation of tooth movement allows the biter to assess whether furthur pressure is likely to injure the tooth or jaw, and to avoid the painful consequences of biting too forcefully on a hard object It is important to have resiliency that not merely protects the integrity of the implant, but allows the feel of a normal tooth.

The present invention provides a simple dental support structure for use in a dental implant. The structure is simple to manufacture and comprises a cylindrical stem having an axis which is moveable against an axially directed resisting force within a guide to provide a prophilactic crown attached to the stem with a degree of movement like that of a natural tooth crown. As a result the prophilactic crown does not have an artificially rigid or fixed relation to the jaw and approximates the movement that a natural tooth is capable of, with some of the attendant advantages discussed above for normal teeth.

It is an object of the present invention to provide a dental support structure mechanism with few internal parts for insertion into an implant comprising a stem moveable within a guide in such a manner that the artificial crown has a freedom of motion resembling that of the crown of a natural tooth which is resisted by an elastic force which is predominately directed upward along the axis of the stem.

It is a further object of the present invention to provide a dental support structure for insertion into rigid engagement with an implant in a jaw, the implant having internal walls adapted to retain the dental support structure, the dental support structure comprising a cylindrical stem having at one end an anchoring portion for an artificial crown, said stem located within a hollow cylindrical guide in said support structure, said stem adapted to closely fit the internal cylindrical walls of the guide, the dental support structure guide retaining the dental post stem in a captured moveable engagement along an axis in opposition to an elastic force along the axis of the stem.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

FIG. 1 is a cut-away view of the dental support structure of the present invention.

FIG. 2 is a cut-away drawing of the dental support structure stem at maximum off axis displacement.

FIG. 3 is a further embodiment of the invention utilizing a elastomeric cap.

DETAILED DESCRIPTION OF A PREFERRED EMBODIMENT

As shown in FIG. 1, a dental support structure 1 is shown which is intended for insertion into a hollow implant 3 in a patient's jaw 5. The support structure has a cylindrical stem 7 comprising an anchoring portion 9 to which an artificial crown 11 may be attached. The implant 3 is designed for implantation into the jaw 5 and may have internal screw threads 13 to engage corresponding threads 15 on the exterior surface of the support structure. The support structure may have grooves or some other irregularity at its top end 17 to permit it to be grasped by a wrench and tightened during insertion into the implant. The entire apparatus has a circular cross-section when seen from a top view (not shown).

The dental support structure comprises a cylindrical structure having a bore, and referred to as a guide 25 which slidably guides the stem 7 permitting motion along the longitudinal axis 19 of the guide. The stem's outside diameter is slightly less than the internal diameter of the guide by approximately 0.1 mm to allow the longitudinal axis of the stem to move to positions not parallel to the longitudinal axis of the guide. (See FIG. 2).

The stem has an indentation 21 which engages a corresponding boss 23 of the guide. This provides a stop which permits axial motion of about 0.1 mm of the stem relative to the guide. The stem may have a split 29 along part of its length to allow it to flex during insertion of the boss into the indentation. See, for example, FIG. 3. This motion along the axial direction is intended to simulate the motion of a natural tooth crown. A pressure exerting means 27 is located within the guide 25. An o-ring 31 is used to prevent the entrance of fluids into the space between the stem and the guide.

The pressure exerting means 27 may constitute a spring or a series of springs or any substances which are elastic, and may be, under suitable conditions, either a biologically safe plastic or rubber.

The effect of a series of springs or other elastic media obeying Hookes' law is the same as a single spring until the limit of compression of one element of the series is reached. At that point, the spring constant suddenly changes to a higher value. This resembles the situation with natural teeth where there are so-called "break" regions, i.e., regions where the compressibility of the structures holding the tooth. This may be understood as follows for a series of springs having force constants $K_1, \ldots K_n$, displacements $X_1, \ldots X_n$, and an overall displacement $Y = X_1 + X_2 + \ldots + X_n$. The Hookes' law potential energy stored in such a system by virtue of the compression of the system is $$V = \Sigma \tfrac{1}{2} K_i X_i^2$$

where force balance requires for each i $$K_i X_i = K_{i+1} X_{i+1}$$

Thus $$X_i = \frac{K_1 X_1}{K_i}$$

and $Y = Y = K_i X_i / K_e$ where $1 K_e = \Sigma \, 1 K_i$. Hence, $$V = \Sigma \frac{1}{2} \frac{K_i K_1^2 X_1^2}{K_i^2}$$

or $$V = \tfrac{1}{2} K_e Y^2$$

Thus the system acts as if it had a single spring with an effective spring constant $K_e$ and total displacement Y. As each spring "bottoms out" $K_i = \infty$, and its contribution to the sum of values which equals $1 K_e$ suddenly becomes zero. Using the relation $1 K_e = \Sigma \, 1/K_i$ it is straightforward to select the spring constants that will give the desired elasticity and breaks. The preferred values should be chosen so that a force of at least 100 pounds and perhaps as much as 400–500 pounds is required to fully compress the resilient material.

Although depicted as a spring located below the bottommost surface of the stem, the spring may extend into a secondary bore (not shown) in the stem. The pressure exerting means may also comprise a pin which bears against the stem. The stem preferably has a large diameter for structural strength, being narrow enough to permit the desired off axis tilt.

As shown in FIG. 3 an elastomeric cap 27 is provided as the pressure exerting means at an extremity of the stem in place of a spring or series of springs. The cap may have a layered structure, where each layer has a different compression modulus.

Further embodiments of the pressure exerting mechanism and its relation to the moveable parts of the dental support structure will be known to persons of skill in the spring pin art.

When implanted in the patient, the device of the present invention has the advantage that the patient feels motion of the crown in a manner which is similar to the feel of natural live teeth. The device is particularly suitable for use with dental implants which are set directly into the jaw bone and do not have the benefit of the natural tooth root to hold the dental support structure In this case, the motion which simulates the situation with actual teeth permits the chewer to sense unusual resistance of objects being bitten into and therefore helps in preventing injury to the jaw and tooth crown.

While there have been shown, described and pointed out the fundamental novel features of the invention as applied to the preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the claims defining the scope of the present invention.

What is claimed is:

1. A dental support structure for insertion into engagement with an implant in a jaw, the implant having internal walls adapted to retain said dental support structure mechanism, said dental support structure mechanism comprising a cylindrical stem having a stem axis and having at one end an anchoring portion for an artificial crown, a cylindrical dental support structure guide having a guide axis adapted to be retained by the internal walls of the implant, said dental support structure guide slidably retaining said stem in an engagement moveable along an axis and capable of unconstrained motion of the axis of said stem with respect to said guide axis, pressure exerting means within said dental support structure guide at an extremity thereof, wherein said stem is capable of axial motions along said guide axis and wherein said pressure exerting means applies a force opposing the motion of said post stem in one direction along said guide axis, and wherein said motion of the axis simulates the motion of the axis of a natural tooth, said dental support structure guide having an internal groove engaging a boss in said dental post stem to stop the motion of said stem axis relative to said guide axis at a predetermined distance along said guide axis, said pressure exerting means having a spring means disposed within said dental support structure guide and comprising a plurality of elastomeric materials having different effective spring constants.

2. A dental support structure for insertion into engagement with an implant in a jaw, the implant having internal walls adapted to retain said dental support structure mechanism, said dental support structure mechanism comprising a cylindrical stem having a stem axis and having at one end an anchoring portion for an artificial crown, a cylindrical dental support structure guide having a guide axis adapted to be retained by the internal walls of the implant, said dental support structure guide slidably retaining said stem in an engagement movable along an axis and capable of unconstrained motion of the axis of said stem with respect to said guide axis, pressure exerting means within said dental support structure guide at an extremity thereof, wherein said stem is capable of axial motions along said guide axis and wherein said pressure exerting means applies a force opposing the motion of said post stem in one direction along said guide axis, said dental support structure guide having an internal groove engaging a boss in said dental post stem to stop the motion of said stem axis relative to said guide axis at a predetermined distance along said guide axis, wherein said pressure exerting means is a spring means disposed within said dental support structure guide, said spring means comprising a plurality of elastomeric materials having different effective spring constants.

3. A dental support structure for insertion into engagement with an implant in a jaw, the implant having internal walls adapted to retain said dental support structure mechanism, said dental support structure mechanism comprising a cylindrical stem having a stem axis and having at one end an anchoring portion for an artificial crown, a cylindrical dental support structure guide having a guide axis adapted to be retained by the internal walls of the implant, said dental support structure guide slidably retaining said stem in an engagement moveable along an axis and capable of unconstrained motion of the axis of said stem with respect to said guide axis, pressure exerting means within said dental support structure guide at an extremity thereof, wherein said stem is capable of axial motions along said guide axis and wherein said pressure exerting means applies a force opposing the motion of said post stem in one direction along said guide axis, and wherein said motion of the axis simulates the motion of the axis of a natural tooth, said dental support structure guide having an internal groove engaging a boss in said dental post stem to stop the motion of said stem axis relative to said guide axis at a predetermined distance along said guide axis, said dental post stem comprising a slit along a portion of its length to enable said boss to move relative to said axis during assembly of said boss into said internal groove.

* * * * *

UNITED STATES PATENT AND TRADEMARK OFFICE
CERTIFICATE OF CORRECTION

PATENT NO. : 5,114,343
DATED : May 19, 1992
INVENTOR(S) : Musikant et al.

It is certified that error appears in the above-identified patent and that said Letters Patent is hereby corrected as shown below:

On Title page, item [19], change "Musikanti et al." to

--Musikant et al. --.

Signed and Sealed this

Thirteenth Day of July, 1993

Attest:

MICHAEL K. KIRK

*Attesting Officer*   *Acting Commissioner of Patents and Trademarks*